United States Patent [19]
Schweitzer, Jr. et al.

[11] Patent Number: 5,584,671
[45] Date of Patent: Dec. 17, 1996

[54] APPARATUS FOR DELIVERING FLUID TO A PATIENT

[75] Inventors: Frederick F. Schweitzer, Jr., Glencoe; Clarence L. Walker, Webster Groves; Randall J. Krohn, Ballwin, all of Mo.

[73] Assignee: Sherwood Medical Company, St. Louis, Mo.

[21] Appl. No.: 345,086

[22] Filed: Nov. 28, 1994

[51] Int. Cl.⁶ .......... F04B 49/00; F04B 39/08; F16K 25/00; A61M 1/00
[52] U.S. Cl. .......... 417/298; 137/454.4; 251/129.11; 417/305; 417/505; 604/151
[58] Field of Search .......... 417/63, 290, 298, 417/305, 505; 137/454.2, 454.4; 251/129.11; 604/151, 152, 153, 154, 155

[56] References Cited

U.S. PATENT DOCUMENTS

| | | | |
|---|---|---|---|
| 3,091,239 | 5/1963 | Moeller | 128/214 |
| 3,097,585 | 7/1963 | Carlson | 95/89 |
| 3,831,625 | 8/1974 | Roediger | 137/377 |
| 3,858,601 | 1/1975 | Ensinger | 137/374 |
| 3,957,082 | 5/1976 | Fuson et al. | 137/625.41 |
| 3,985,133 | 10/1976 | Jenkins et al. | 128/214 F |
| 4,219,021 | 8/1980 | Fink | 128/214 B |
| 4,460,358 | 7/1984 | Somerville et al. | 604/250 |
| 4,557,725 | 12/1985 | Heyne et al. | 604/151 |
| 4,585,411 | 4/1986 | Bocci et al. | 604/245 |
| 4,585,442 | 4/1986 | Mannes | 604/250 |
| 4,604,093 | 8/1986 | Brown et al. | 604/248 |
| 4,689,043 | 8/1987 | Bisha | 604/250 |
| 4,884,013 | 11/1989 | Jackson et al. | 318/481 |
| 5,005,604 | 4/1991 | Aslanian | 604/32 |
| 5,017,192 | 5/1991 | Dodge et al. | 604/250 |
| 5,057,081 | 10/1991 | Sunderland | 417/63 |
| 5,156,186 | 10/1992 | Manska | 137/556 |
| 5,219,327 | 6/1993 | Okada | 604/34 |
| 5,242,407 | 9/1993 | Struble et al. | 604/151 |
| 5,244,463 | 9/1993 | Cordner, Jr. et al. | 604/151 |
| 5,364,364 | 11/1994 | Kasvikis et al. | 604/151 |
| 5,374,251 | 12/1994 | Smith | 604/151 |

OTHER PUBLICATIONS

Ross Laboratories, "Flexiflo® Quantum™ Enteral Pump" Operating Manual, 1992, pp. 1–19.
Ross Laboratories, "Flexiflo® Quantum™ Enteral Pump" Instructions for Use, Mar. 1992, two pages.
EntraCare Corp., "UltraFlo™" information page, date unknown, one page.
Sherwood Medical Company, "Ross Quantum Pump" Bulletin, Nov. 11, 1992, pp. 1–4.
"Ross Clinical Study BD28 Enteral Nutrition Pump Performance and Efficacy Study" Operating Manual, Jun. 1991, pp. 1–12.

Primary Examiner—Charles G. Freay
Attorney, Agent, or Firm—Gene B. Kartchner; Montgomery W. Smith

[57] ABSTRACT

A fluid delivery system is disclosed which includes a pump and a fluid delivery set. The fluid delivery set includes a stop cock valve, and the pump includes a valve actuation unit into which the stop cock valve is positioned for operation of the system. The valve actuation unit includes a valve receiving mechanism which requires the valve to be closed in order to be inserted into or removed from the valve actuation unit, thereby preventing accidental free flow of fluid at all times. The fluid delivery set may also include an auxiliary fluid source to allow periodic flushing of the fluid delivery line, and the valve actuation unit can be programmed by the pump to automatically initiate periodic flushing cycles if desired.

24 Claims, 7 Drawing Sheets

*FORWARD ROTATION*

*RETURN ROTATION*

APPARATUS FOR DELIVERING FLUID TO A PATIENT

BACKGROUND OF THE INVENTION

1. Field of the Invention

This invention relates to a system for delivering medical fluids to a patient. More particularly, the present invention relates to an apparatus including an infusion set and a peristaltic pump for delivering enteral nutrition fluids to a patient.

2. Prior Art

Accurately controlled volumetric delivery rates of enteral nutrition fluids to a patient have been accomplished in the past by means of a delivery system which includes a motorized pump and a disposable fluid delivery set. In these systems, delivery of enteral fluids is controlled by regulating the speed of the pump motor in accordance with the desired volumetric flow rate. An example of this type of fluid delivery system is shown in U.S. Pat. No. 4,884,013 issued to Jackson et al.

Although prior art fluid delivery systems such as described above are very useful in accurately delivering fluid to a patient, a disadvantage of such systems is their inability to ensure that free-flow through the fluid delivery set is prevented when the fluid delivery set is being attached or detached from the pump. Another disadvantage is their inability to easily pass flushing fluid through the fluid delivery set on command, or automatically at predetermined intervals, in order to keep blockage from occurring in the flow lines of the fluid delivery set.

OBJECTS AND SUMMARY OF THE INVENTION

A primary object of the present invention is to provide a fluid delivery system which incorporates anti-free flow features into the pump and fluid delivery set thereof to prevent inadvertent free-flow of fluid through the flow lines of the fluid delivery set during attachment and detachment thereof from the pump.

A further object of the present invention is to provide a fluid delivery system which includes a fail-safe system which will prevent free-flow of fluid through the fluid delivery set in the event of mechanical malfunction or power loss of the pump.

Another object of the present invention is to provide a fluid delivery system which allows for automatic or on demand flushing of the delivery set to keep blockages from occurring in the flow lines thereof.

It is further an object of the present invention to provide a fluid delivery system in which the pump is automatically activated for operation when the fluid delivery set is properly attached thereto.

A further object of the present invention is to provide a fluid delivery system in which the fluid delivery set thereof is completely primed for use by the pump, without the need of operator intervention.

Another object of the present invention is to provide a pump having a fluid delivery set interface which is easy to clean between uses.

These and other objects and advantages of the present invention are realized in a preferred embodiment of a fluid delivery system which comprises a fluid delivery set and a pump, which includes a pumping unit and a valve actuation unit which is preferably attachable to the housing of the pumping unit. The fluid delivery set includes a stop cock type valve which has a handle which can be rotated by the valve actuation unit to a series of predetermined positions for fluid flow connection of a desired inlet fluid flow line with the outlet fluid flow line of the delivery set. The handle of the valve must be oriented in its fully closed position in order to be inserted into a similarly shaped opening in the fluid delivery set interface of the valve actuation unit and be accepted by the valve receiving mechanism thereof for operation. Because the delivery set interface will only allow attachment of the valve to the actuation unit when the valve is in its completely closed position, inadvertent fluid flow through the delivery set during attachment is prevented.

Proper positioning of the valve into the delivery set interface of the actuation unit positions the valve handle into the valve handle receiving mechanism where it can be rotated by the rotating chuck of the receiving mechanism during operation.

The valve actuation unit and the pumping unit are preferably controlled by a single central processing unit which is automatically activated by the proper attachment of the valve to the actuation unit. The initial action of the pump when activated is to lock the handle in place within the valve receiving mechanism for use by initiating a slight rotation of the valve handle receiving chuck. The valve is locked in position within the valve receiving mechanism and cannot be detached therefrom at any time in which the valve handle is in a rotational position which can allow fluid to flow through the valve. When it is desired to remove the valve from the pump, the valve receiving mechanism of the pump rotates the stop cock valve handle to its fully closed position and automatically ejects the valve from the receiving mechanism.

The stop cock valve preferably is designed to allow the fluid delivery set of which it is a part to include more than one input fluid flow line for alternative access to the outlet fluid flow line thereof if desired. In this manner, a secondary fluid container can be included as part of the fluid delivery set which preferably contains flushing fluid which can be pumped through the outlet fluid flow line to flush the primary enteral nutrition fluid therefrom on a periodic basis to prevent the outlet fluid flow line from becoming clogged by enteral nutrition fluid.

The pump further is preferably programmed with a priming operation which is initiated upon proper attachment of the fluid delivery set including the stop cock valve thereto, and which completely primes the outlet fluid flow lines as part of an initial setup operation.

The chuck of the valve receiving mechanism is spring mounted for axial movement along a spindle of an electric motor. Proper insertion of the handle of the stop cock valve into the receiving mechanism forces the chuck against the spring and moves it to a compressed position over the spindle. In its compressed position, the chuck activates a switch which signals the central processing unit of the pump to commence the automatic locking and initial set up operation.

The above and other objects and advantages of the present invention will become apparent from the following more detailed description, when taken in conjunction with the accompanying drawings in which like elements are identified with like numerals throughout.

DETAILED DESCRIPTION OF THE PREFERRED EMBODIMENT

Figure 1:
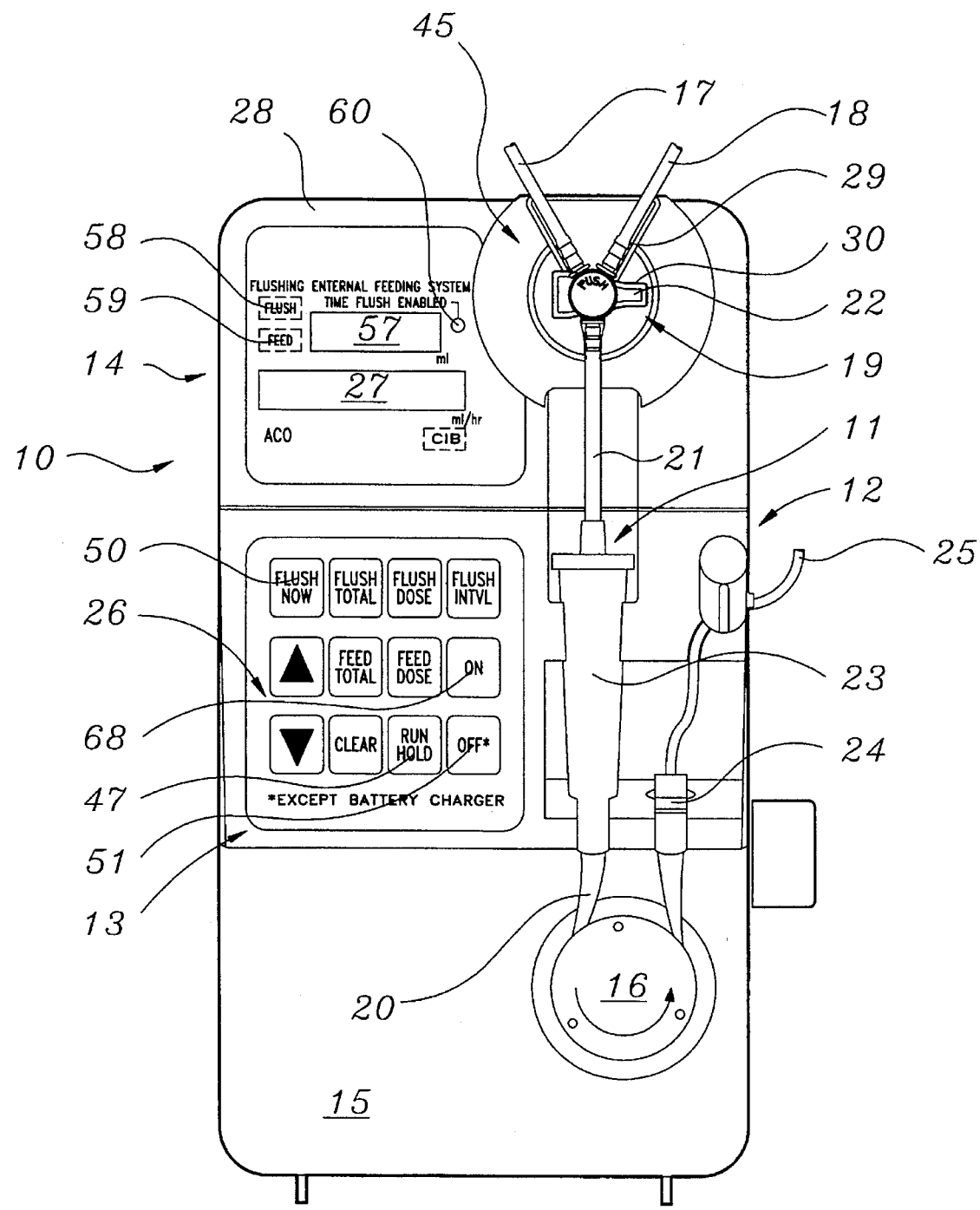
FIG. 1 is a plan elevation view of a preferred embodiment fluid delivery system made in accordance with the principles of the present invention.

As shown in the exemplary drawings for the purposes of illustration, an embodiment of a fluid delivery system made in accordance with the principles of the present invention, referred to generally by the reference numeral 10, is provided for anti-free flow attachment and detachment of a fluid delivery set with a pump which includes the capability for automatic priming, and automatic or on demand flushing of the outlet fluid flow line of the fluid delivery set.

More specifically, FIG. 1 is an illustration of a fluid delivery system 10 formed in accordance with the present invention which includes a pump 12 and a disposable fluid delivery set 11 attached thereto for operation. The pump 12 includes a pumping unit 13 and a valve actuation unit 14. The pumping unit 13 includes a housing 15 through which protrudes a pump rotor 16. The rotor 16 is driven by a conventional DC motor and controlled by a central processing unit (not shown) in a well known manner, such as is described in U.S. Pat. No. 4,884,013 issued to Jackson et al., which is incorporated herein by reference.

The fluid delivery set 11 preferably includes a pair of inlet fluid flow lines comprised of inlet tubes 17 and 18 which are connected to fluid containers (not shown) which contain fluids to be delivered through the fluid delivery set 11 to the patient. The fluids are preferably enteral feeding fluid and flushing fluid. The inlet tubes 17 and 18 are connected at their ends opposite the fluid reservoir containers to a stop cock valve 19 which controls the passage of fluid from the inlet tubes 17 and 18 to an outlet fluid flow line.

The stop cock valve 19 of the fluid delivery set 11 comprises a handle 22 and body 66 which are shaped to allow attachment of the valve 19 to the valve actuation unit 14 in a single unique orientation, corresponding to the closed position of the valve 19 in which fluid flow therethrough is prevented.

The outlet fluid flow line of the fluid delivery set includes an outlet tube 21, a drip chamber 23, a pump tube 20, and a patient connector tube 25. The pump tube 20 surrounds the pump rotor 16 in use, and is preferably formed of an elastic material such as silicone. Rotation of the rotor 16 in the direction indicated by the arrow in FIG. 1 causes the pumping tube 20 to pump fluid into the patient connector tube 25 at a rate which is determined by the rate of rotation of the rotor 16.

The outlet tube 21 is connected to drip chamber 23 which is mounted in a recess in the housing 15 of the pumping unit 13 and secured to the inlet end of the pump tube 20. The outlet end of the pump tube 20 is provided with a mounting member 24 which is received in another recess in the pumping unit housing 15 to thereby secure the outlet end of the pump tube 20 to the pump 12, and to maintain the pump tube 20 properly stretched over the rotor 16 for operation. The patient connector tube 25 is connected to the outlet end of the pump tube 20 and delivers fluid from the fluid delivery system 10 to the patient, either directly, or through connection to a tube previously prepared for the patient such as a nasogastric, gastrostomy, or jejunostomy tube.

The pumping unit 13 includes an interactive control pad 26 mounted in the housing 15 thereof which allows an operator to set various functions of the system 10, such as flow rate and dose (total volume) of feeding fluid to be delivered to the patient, interrupt operations of the pump unit 13, and an increase or decrease in the designated feed dose volume or feeding fluid flow rate. Similarly, the control pad 26 allows the operator to set the flushing fluid dose and time period between each flushing cycle, or to initiate an immediate flush cycle at any time. However, the flushing fluid flow rate is preferably preset and therefore not intended to be controlled by the operator. The operation and internal workings of the pumping unit 13 of the present invention are thoroughly described in the above-mentioned U.S. Pat. No. 4,884,013.

The valve actuation unit 14 of the pump 12 is enclosed within an actuation unit housing 28. The valve recess 29 which is shaped to receive the stop cock valve 19, the inlet tubes 17 and 18, and the outlet tube 21 in a single unique orientation (as shown in FIG. 1) is included in a valve interface 45 which is detachable from the housing 28 for cleaning when necessary. The interface 45 forms a handle opening 30 which passes through the bottom of the valve recess 29 thereof. The handle opening 30 passes completely through the interface 45 to allow access of the valve handle 22 to the valve receiving mechanism 32 within the housing 28. The handle opening 30 is nearly identical in shape to the valve handle 22, so that, only proper alignment of the handle 22 with the handle opening 30 will allow the handle 22 to pass into or out of the housing 28. As will be explained in more detail below, the valve recess 29 and handle opening 30 force a single unique orientation of the valve handle 22 with respect to the valve body 66 before the inlet tubes 17 and 18 and the outlet tube 21 can be received within the valve recess 29 and the handle 22 can pass through the handle opening 30 for purposes of attachment. This single unique orientation of the valve handle 22 with respect to the remainder of the valve 19 corresponds to the fully closed position of the valve 19. In this manner, as is clearly evident, the valve 19 cannot be loaded into the actuation unit 13 of the pump 12 for use, nor more importantly, removed from the actuation unit 13 at any time, unless the handle 22 thereof is in its fully closed position. This of course prevents accidental fluid flow through the fluid delivery set 11 during loading thereof for use, and prevents ejection of the valve 19 from the actuation unit at any time without first closing the valve 19 against fluid flow.

Figure 2:
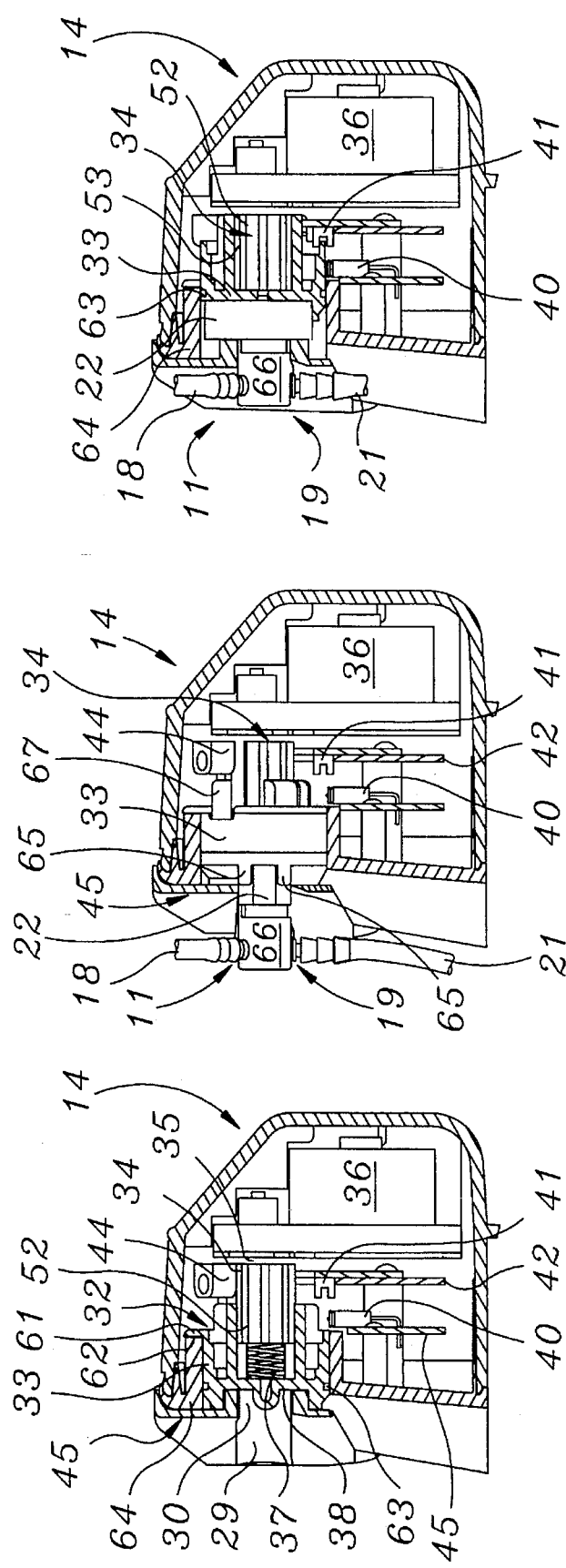
FIGS. 2a–c are partial cross-sectional views of the valve of the fluid delivery set and the valve actuation unit of the pump of the fluid delivery system of the present invention.

As shown in FIGS. 2a–2c, when the valve handle 22 is passed through handle opening 30, it immediately contacts the chuck 33 of the valve receiving mechanism 32. The chuck 33.is mounted to a spline 34 which is in turn mounted to the rotating shaft 35 of a stepper motor 36. The chuck 33 is limited to translational movement over the spline 34 by the spline ridges 52, and corresponding chuck grooves 53. The chuck 33 is biased by the spring 37 to an extended position in which the chuck face 38 thereof rests against the interior surface 46 of the interface member 45, located around the valve opening 30 thereof.

Continued movement of the valve 19 into the valve recess 29 causes the valve handle 22 to force the chuck 33 against the spring 37 and along the spline 34. The chuck 33 will slide over the spline 34 a sufficient distance to ensure that the valve handle 22 can pass entirely through the handle opening 30 into the cylindrical recess 64.

As the chuck 33 approaches its fully compressed position, the outer surface of the chuck 33 contacts the microswitch 40 to automatically activate the microprocessor of the pump 12. Continued compression of the chuck 33 causes a control flange 39, which extends rearwardly from the chuck 33, to operationally engage with photoelectric switches 41, 48 and 49. This initiates rotation of the stepper motor 36 to rotate the chuck 33 a predetermined rotational distance. Since the valve 19 is held in a fixed unique orientation with respect to the valve interface 45 by the valve recess 29, and the valve handle 22 is fixed in the chuck face 38 by the handle positioning stubs 65, the handle 22 is forced to rotate in response to rotation of the chuck 33 by the stepper motor 36. The predetermined automatic initial rotation of the chuck 33 therefore causes the valve handle 22 to become trapped against the interior surface 46 of the interface member 45.

Figure 3:
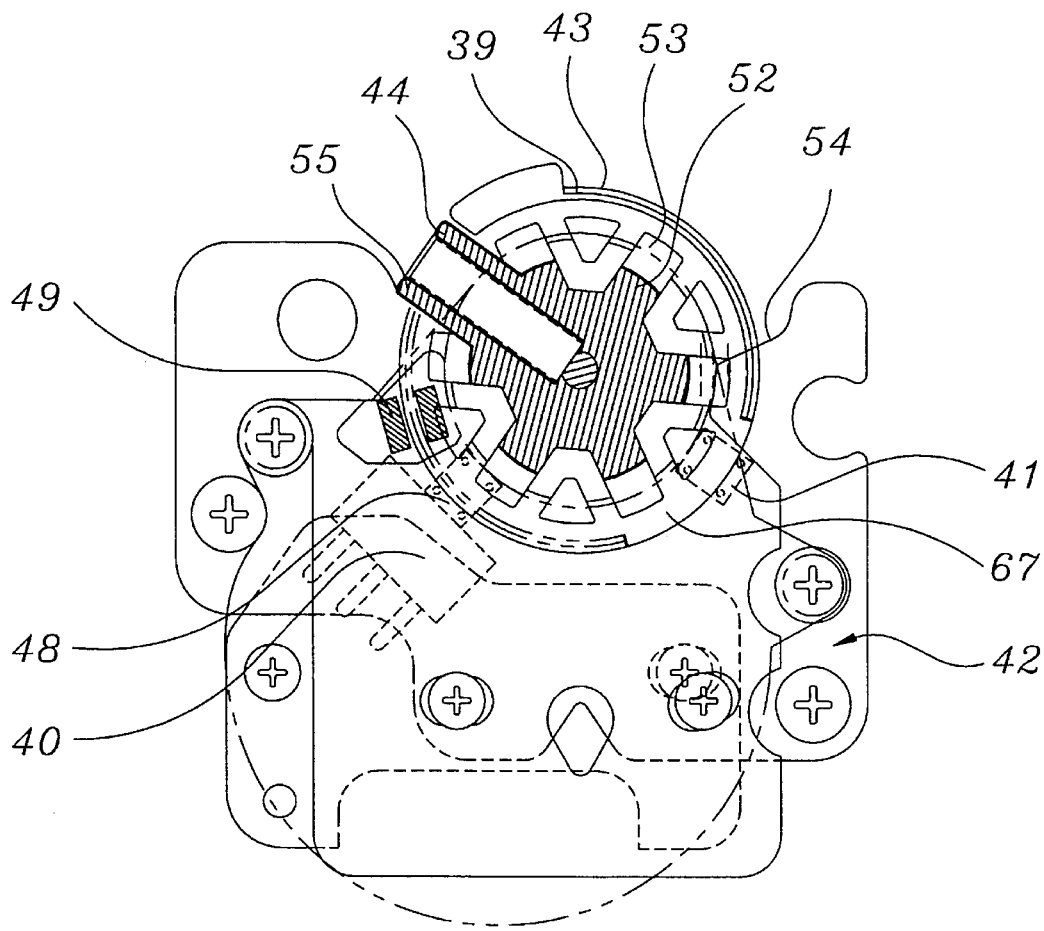
FIG. 3 is a rear view of the valve receiving mechanism motor and sensor monitoring plate made in accordance with the principals of the present invention.

As best shown in FIG. 3, the control flange 39 is positioned on the chuck 33 so as to pass through the series of photo-electric switches 41, 48 and 49 as the chuck 33 is rotated by the stepper motor 36. The photo-electric switches 41, 48 and 49 are mounted on a control plate 42 around an arcuate path followed by the control flange 39. The photo-electric switches 41, 48 and 49 send electrical signals to the central processing unit of the pump 12, signalling the presence or absence of the control flange 39 therein in an operational manner which identifies the rotational position of the chuck 33, and thus the valve handle 22, to the central processing unit. In this manner, electrical commands sent to the stepper motor 36 to rotate the chuck 33 (and thusly the handle 22 of the valve 19) are controlled by the actual rotational position (orientation) of the flange 29 of the chuck 33 as monitored by the central processing unit using the photo-electric switches 41, 48 and 49 as the monitoring devices, creating a closed loop electrical system for operating the valve receiving mechanism 32.

If desired, the microswitch 40 can also be utilized in providing feedback information to the central processing unit of the pump 12 relating to the position of the chuck 33 during pump operation. This can be accomplished by the positioning of one or more notches 43 at predetermined radial positions around the cylindrical surface of the chuck 33 to trigger the microswitch 40 each time a notch 43 is rotated therepast during operation. When a notch 43 passes the microswitch 40, it leaves sufficient space to allow the microswitch to release thereinto, and then re-trigger when the notch 43 passes. Each release or retriggering of the microswitch 40 sends a signal to the central processing unit of the pump in the manner well known to those skilled in the art of microswitch operation. Each notch 43 can be formed to entail as much of a radial arc around the chuck 33 as desired for the proper positional operation of the chuck during use. As is evident therefor, the microswitch 40, or a series of similar microswitches, could be used to replace one or more photoelectric switches if properly positioned to maintain the same signal logic sequence for the replaced photoelectric switches, as will be described below. Similarly, the microswitch 40 could be replaced with an equivalent switch such as a photoswitch, magneto resistive switch, etc.

The total angle of rotation through which the valve handle 22 can be rotated in the valve body by the receiving mechanism 32 is limited by the governor tab 44 on the spline 34. The governor tab 44 interferes with the stop surfaces 54 and 55 on the motor/sensor monitoring plate 42 at each end of its predetermined maximum rotational arc to prevent accidental over rotation of the valve handle 22, and to assist in resetting the chuck in its starting position if positional errors occur during operation. The preferred predetermined maximum valve rotation allowed by the governor tab 44 and stop surfaces 54 and 55 is approximately 120degrees.

Figure 4:
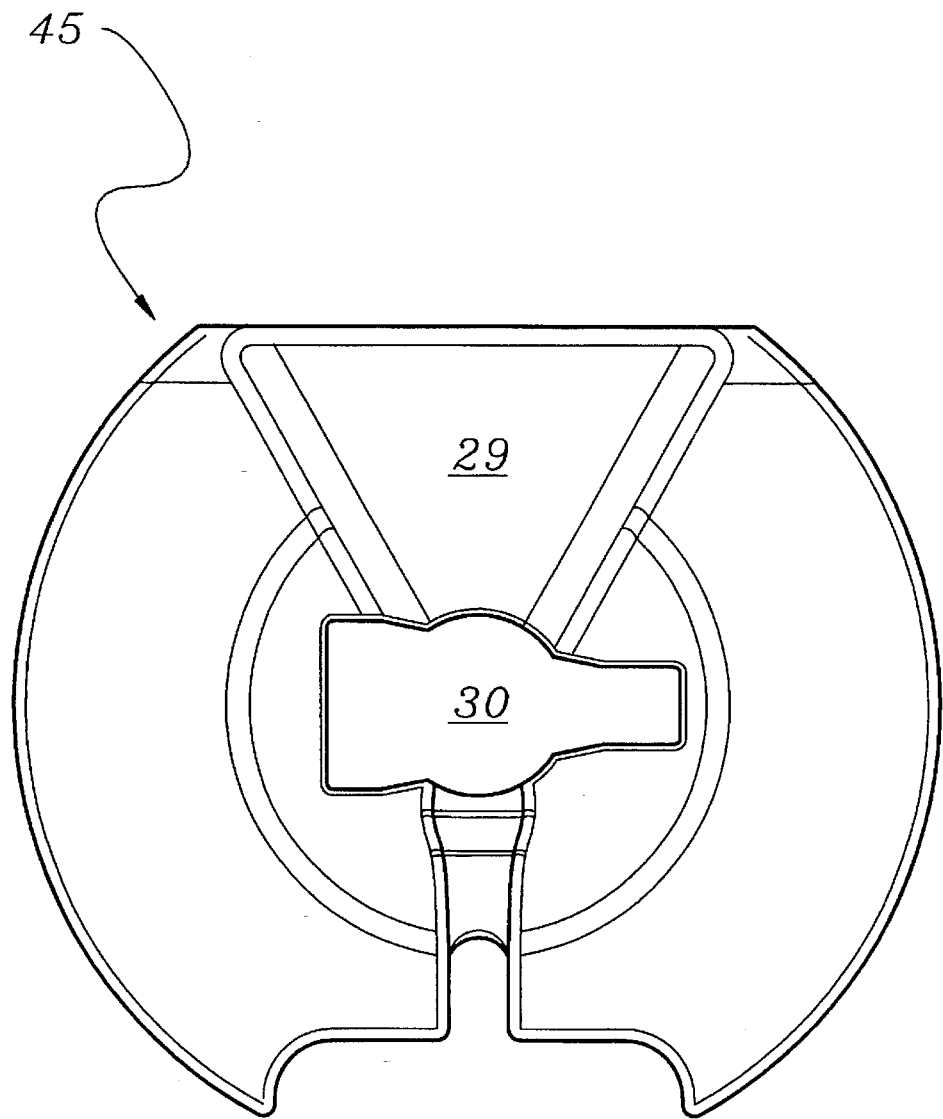
FIG. 4 is a front view of the disc-shaped valve interface member of the preferred embodiment of the present invention detached from the valve actuation unit of the pump.
Figure 5:
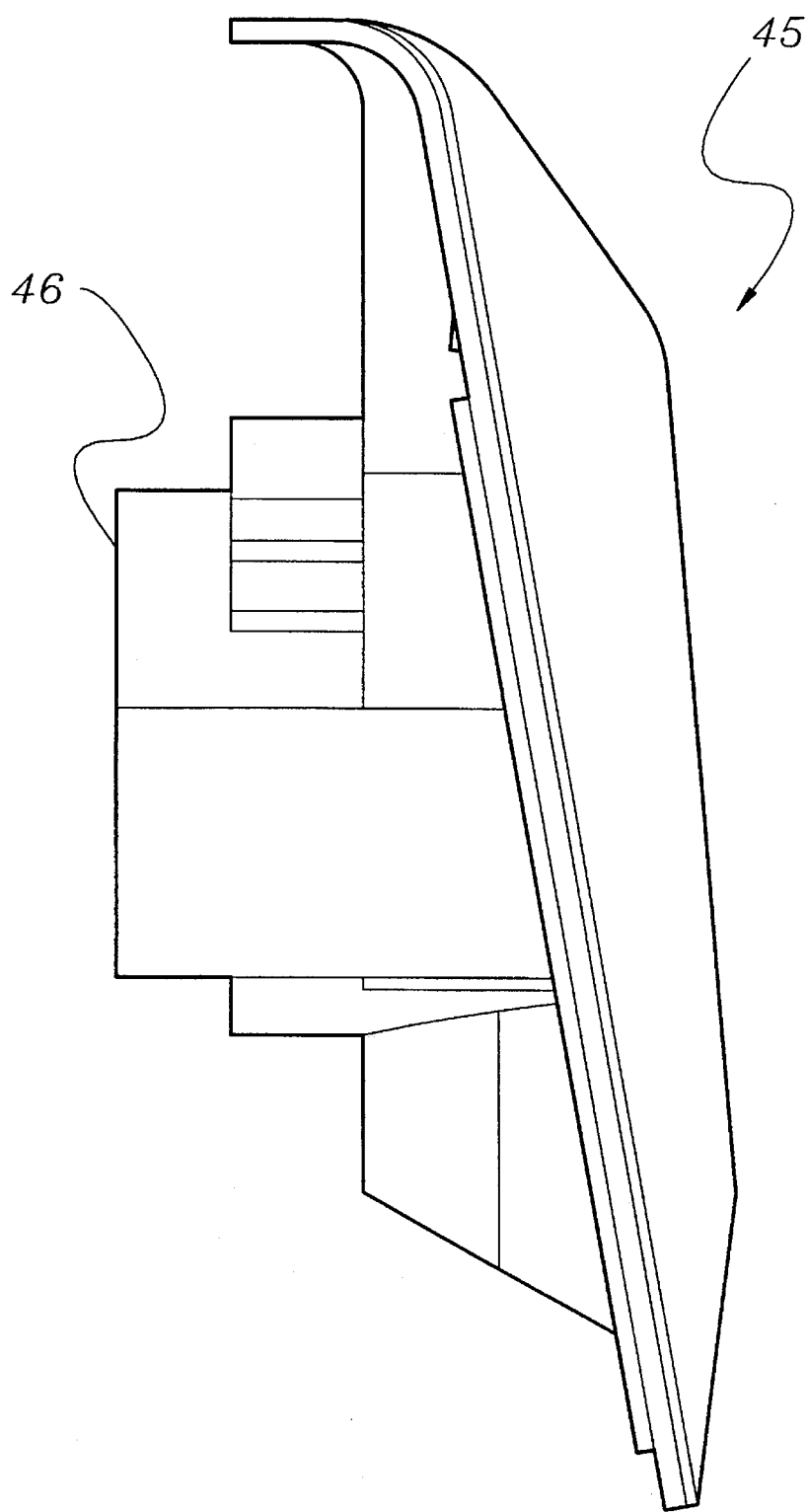
FIG. 5 is a side view of the disc-shaped valve interface member shown in FIG. 4.
Figure 6:
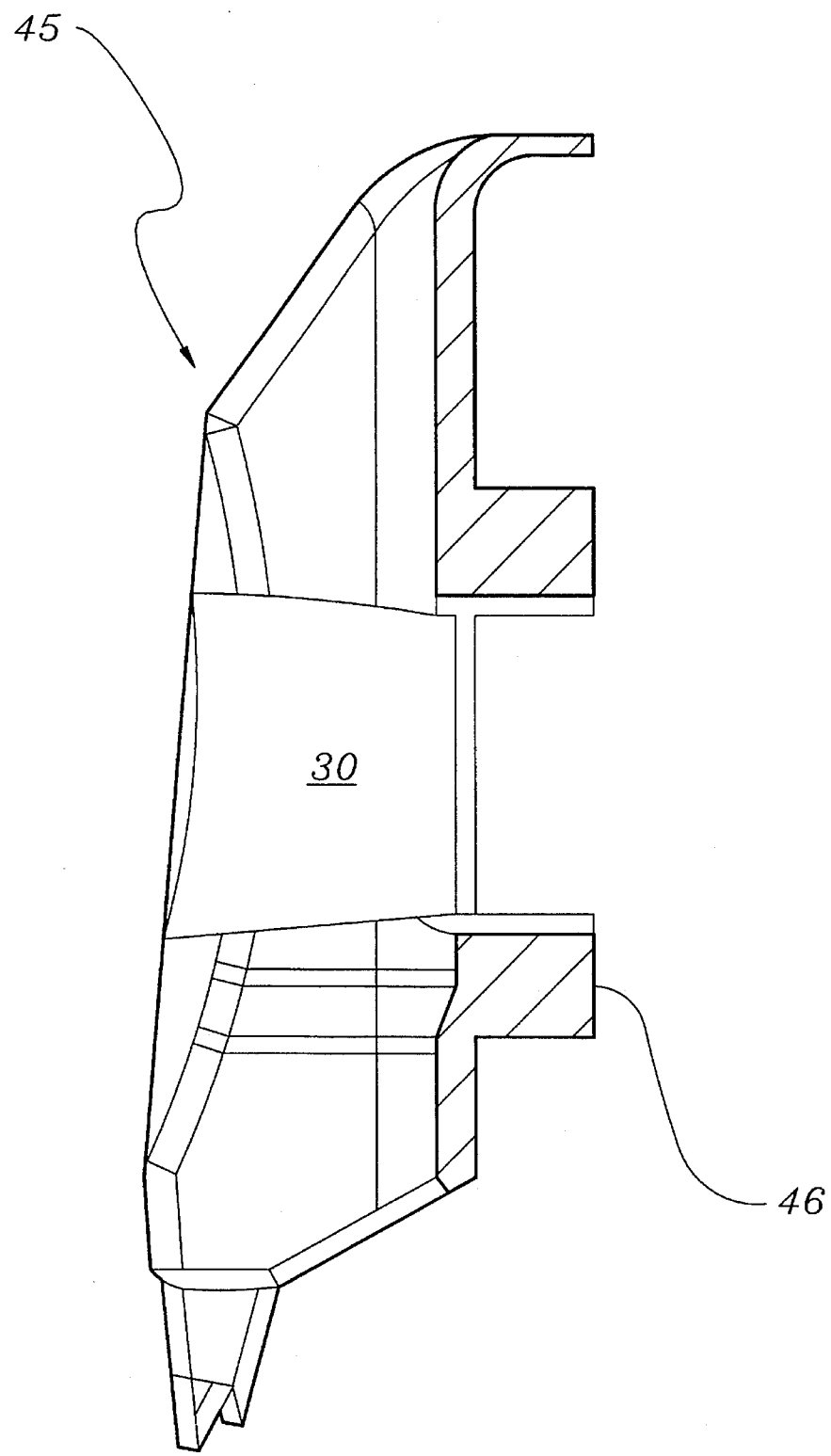
FIG. 6 is a cross-sectional view of the disc-shaped valve interface member taken along line V—V of FIG. 4.

As is best shown in FIGS. 1 and 4–5, the disc-shaped valve interface member 45 may be detachable from the actuation unit housing 28 by means of screws or the like (which may pass through the back of the housing 28 and are not shown) to allow cleaning thereof when necessary. Removal of the interface member 45 from the housing 28 also exposes the chuck face 38 for cleaning if desired. When the interface member 45 is removed from the housing 28 for cleaning, the chuck 33 remains held in position within the cylindrical housing extension 64 by the stop tab 61 which extends to contact the housing stop surface 62 to stop outward movement of the chuck 33 (see FIG. 2). In this manner, the sealing engagement between the chuck cup-type seal 63 and the cylindrical housing extension 64 is maintained so that fluid which may be present at the chuck face 38 cannot pass into the housing 28.

When the interface member 45 is replaced on the housing 28, the interior surface 46 thereof pushes the chuck 33 a small distance away from the housing 28 to disengage the chuck stop tab 61 from the housing stop surface 62. In this manner, the valve handle 22, when in position in the chuck 33, rotates only against the interior surface 46 of the interface member 45 and is not interfaced with by the housing 28. The chuck 33 includes a cup-type seal gasket 63 which forms a seal between the chuck and the cylindrical housing extension 64 and prevents the passage of fluid past the chuck 33 into the interior of the valve actuation unit 14.

OPERATION OF THE PREFERRED EMBODIMENT

To operate the fluid delivery system 10 of the present invention, the operator attaches a fluid delivery set 11 to the pump 12 as shown in FIG. 1. This can be accomplished by inserting the drip chamber 23 into the proper recess in the pump unit housing 15 and stretching the pump tubing 20 around the pump rotor 16. The mounting member 24 is then inserted in its own recess in the pump unit housing 15 where its presence is sensed by a sensor (not shown) which signals the pump 12 that the outlet flow line has been properly positioned thereon. The fluid containers in fluid flow attachment with the inlet tubes 17 and 18 are preferably suspended above the pump 12 in a well known manner.

The operator then ensures that the handle 22 of the stop cock valve 19 is in its fully closed position, and inserts the valve 19 into the valve recess 29 of the interface member 45 until the handle 22 thereof passes through the handle opening 30 and engages the face 38 of the chuck 33. If desired, the valve 19 of the fluid delivery set may be manufactured and supplied to the operator in its closed position to prevent free flow through the valve 19 at all times prior to use. The valve 19 may also include a safety tape positioned therearound to discourage rotation of the valve handle 22 from its closed position, which must be removed by the operator prior to attachment of the valve 19 to the valve actuation unit 14.

The operator continues to force the valve 19 inwardly against the bias of the spring 37 until the chuck 33 actuates the microswitch 40 (which activates the microprocessor) and the control flange 39 thereof is positioned within the photoelectric switches 41, 48 and/or 49 for operation. In this position, referred to hereinafter as the "starting position" the valve handle 22 has moved completely within the housing 28. After actuation of the microswitch 40 and operational engagement of the control flange 39 in the photoelectric switches 41, 48 and 49, the stepper motor automatically rotates an initial approximately 30 degrees from its starting position, which causes the valve handle 22 to be trapped against the interior surface 46 of the interface member 45. This new position is the "initial locking position" of the valve handle 22 within the actuation unit housing 28. The initial locking position of the valve 19 does not open any fluid flow path therethrough.

If desired, the operator may manually actuate the on button 68 before loading the fluid delivery set 11 into the pump 12, however, no pump action will occur until the fluid delivery set is actually loaded.

Once the microswitch 40 has been triggered to activate the microprocessor, the microprocessor in turn initiates activation of the upper and lower displays 57 and 27 respectively. The upper display 57 is preferably smaller than the lower display 27 and is used primarily to display a running total of fluid delivered, either flushing fluid or feeding fluid, so that progress towards the programmed total feeding fluid dose or total flushing fluid dose can be monitored by the operator. The adjacently positioned flushing light 58 and feeding light 59 illuminate in turn to correspond to the particular accumulated fluid volume showing in the display 57 as will be explained in more detail below. The lower display 27 is used for displaying more general information and to assist the operator in programming and operating the system 10. The lower display 27 will display any preprogrammed parameters which have been entered from the key pad 26 and also scroll through messages relating to the immediate operation being performed by the pump 12. Operation of the lower display 27 will also be explained in more detail below.

Once the valve handle 22 has been rotated to the initial locking position, the microprocessor immediately illuminates the flushing light 58 and causes the upper display 57 to display the accumulative volume delivered of flushing fluid (starting with zero, since no fluid has yet been delivered by the pump 12). The lower display 27 will initially provide no information to the operator since the operator has input no programming information at this point through the key pad 26.

However, it is a preferred embodiment of the present invention that the pump 12 also include memory capabilities which allow it to store operational parameters which were previously input by an operator, and automatically retrieve to the preprogrammed operational parameters upon initial attachment of a fluid delivery set 11 to the pump 12. Also if desired, the automatic retrieval of preprogrammed parameters may be time limited so that only preprogrammed information received by the pump 12 within a predetermined time period will be retrieved to and any time period greater than the time limited period will clear those values and force the operator to re-input the desired parameters. A preferred time period for automatic retrieval to preprogrammed parameters is approximately 16 hours.

If non-zero preprogrammed parameters are retrieved to by the pump 12 at the initiation of a new operation cycle, the parameters are presented in the lower display 27. Otherwise, the operator inputs the desired parameters through the key pad 26 at a later time as will be explained.

Next, the pump 12 initiates rotation of the stop cock handle 22 an additional approximately 30 degrees to the "flushing position", which is approximately 60 degrees from the starting position, after an additional actuation of the run/hold key 47, and makes fluid flow connection between the inlet tube 18 and the outlet tube 21. The pump rotor 16 then draws flushing fluid from the flushing fluid container, through the inlet tube 18, and into the drip chamber 23 where the pump detects the presence of drops ensuring proper fluid flow through the fluid delivery set 11.

Once the drop detection is complete, the valve handle 22 automatically rotates an additional 60 degrees to the "feeding position" which is approximately 120 degrees from the starting position.

This opens fluid flow communication between the inlet tube 17 and the outlet tube 21. Priming is then commenced by the pumping unit 13 pumping enteral fluid from the enteral fluid container through the inlet tube 17 and the outlet tube 21 into the drip chamber 23 where it is sensed by the drip sensor (not shown). After completion of the enteral fluid priming, a leak test is then performed by initiating rotation of the rotor 16 by the pump 12 back 30 degrees to the "temporary off position", which is 90 degrees from the starting position. If drops continue through the drip chamber 23 and are detected by the drip sensors of the pump 12 when the handle 22 is in the temporary off position, it is assumed by the microprocessor that the valve 19 is defective. The handle 22 therefor automatically rotates back to the starting position which allows the spring 37 of the valve receiving mechanism 32 to eject the valve 22 from the handle opening 30. The lower display 27 then automatically displays the phrase "bad set".

To recommence operation of the fluid delivery system 10, the operator thereafter must remove the defective fluid delivery set 11 and replace it with a new fluid delivery set 11 and re-initiate pump operation by inserting the fluid delivery set stop cock valve 19 into the pump's valve receiving mechanism 32.

However, if the leak test is successful, the pump 12 rotates once more to the feeding position and continues to pump enteral fluid through the fluid delivery set 11 until the entire outlet fluid flow line of the set is filled with feeding fluid. It is preferred that the priming operation to fill the outlet fluid flow line with feeding fluid be performed at the flushing flow rate in order to speed up the priming process. While priming, the lower display 27 indicates that the priming operation is in progress by displaying the phrase "filling set" for all phases of priming.

Once the outlet fluid flow line of the fluid delivery set 11 is completely primed, the priming operation automatically stops by stopping the rotor 16 and the pump 12 rotating the valve handle 22 in the reverse direction a distance of 30 degrees to the temporary off position. The operator then connects the patient connector tube 25 to the patient for feeding, and enters the desired total feed dose and desired feeding flow rate on the key pad 26. The operator also enters a desired flush dose, and the desired time interval between each flushing cycle initiation. Once this is complete, the automatic flush enabled light 60 illuminates, and remains illuminated until the entire feeding cycle is completed or until the automatic flushing feature is disabled by the operator. The flushing flow rate is preferably fixed by the pump 12 at 1000 ml/hr and is therefore not entered by the operator.

The operator then presses the run/hold button 47 and the fluid delivery system 10 begins delivery of feeding fluid to the patient at the desired feeding flow rate. The feeding flow rate is automatically displayed in the lower display 27, and the cumulative delivered feeding fluid volume is shown in the upper display 57. The feeding light 59 is illuminated to signal the operator that feeding fluid is being delivered to the patient.

Periodically, at each predetermined flush interval (minus the time required to pump the volume of the outlet fluid line at the feeding fluid flow rate), the pump 12 causes the valve handle 22 to be rotated to the flushing position to stop enteral feeding fluid flow from inlet tube 17, and open a flushing fluid flow path from inlet tube 18. Simultaneously, the flushing light 58 begins flashing (while the feeding light 59 remains on), indicating that a flushing cycle has commenced but feeding fluid is still being delivered to the patient at the feeding fluid flow rate. The pump continues to pump at the programmed feeding fluid flow rate until the entire outlet fluid flow line of the delivery set 11 is filled with flushing fluid (i.e., until all of the feeding fluid in the outlet fluid flow line has been fed to the patient). Then, the pump automatically begins pumping flushing fluid at the predetermined flushing fluid flow rate. The lower display 27 displays a scrolling dashed line at this time. Simultaneously, the flushing light 58 is continuously illuminated and the feeding light 59 goes off. The upper display 57 then begins showing the cumulative flushing fluid volume as it is being delivered.

Once the programmed flush dose minus the volume of the outlet fluid flow line has been delivered to the patient, the valve 22 again rotates to the feeding position to stop flow of flushing fluid from inlet tube 18 and open flow of feeding fluid from inlet tube 17. Feeding fluid is then delivered at the predetermined flushing fluid flow rate until the entire outlet fluid flow line is filled with feeding fluid (i.e., until all of the flushing fluid has been delivered to the patient). Simultaneously, the feeding light 59 flashes, and the flushing light 58 remains on, indicating that feeding is about to recommence but flushing fluid is still being delivered to the patient at the flushing fluid flow rate. Once the outlet fluid flow line is completely reprimed with feeding fluid, the pump 12 then automatically begins delivering feeding fluid at the programmed feeding fluid flow rate which is displayed in the lower display 27, and the feeding light 59 is continuously illuminated and the flushing light 58 goes off. The upper display 57 then again shows the cumulative feeding volume as it is being delivered to the patient.

If at any time the operator desires to initiate a flushing cycle, regardless of the status of the preprogrammed autoflushing cycles, the operator need only push the run/hold button 47 and the "flush now" button 50 located on the key pad 26. The lower display 27 then requests the operator to input a flush dose by displaying the phrase "flsh dose". The operator enters the desired flush dose and again pushes the flush now button 50 and the newly programmed flushing cycle commences immediately.

If it is desired to halt operation of the pump at any time, the operator presses the run/hold button 47. In response, the pump 12 initiates rotation of the handle 22 to the temporary off position and halts rotation of the rotor 16. It should be noted that the handle 22 is not rotated to the starting position when the run/hold button 47 is pressed, since this will release the handle 22 from its entrapment behind the valve interface member 45 resulting in ejection of the valve handle 22 from the handle opening 30 by the force of the spring 37 of the valve receiving mechanism 32.

Whenever an operational error such as a flush or feed flow alarm occurs, the pump will automatically move the valve handle 22 to its temporary off position and stop the rotor 16. Once the problem is resolved, the operator presses the run/hold button 47 and operation of the fluid delivery system 10 will resume.

Once the system 10 has delivered the total desired volume of feeding fluid to the patient, (if a total dose was programmed by the operator) the pump 12 automatically moves the valve handle 22 to the temporary off position and signals the operator of the completion of fluid delivery. At any time, the operator can push the off key 51 and the valve receiving mechanism 32 will rotate the valve handle 22 to the starting position and the spring 37 will eject the valve 19 from the valve recess 29.

Figure 7A:
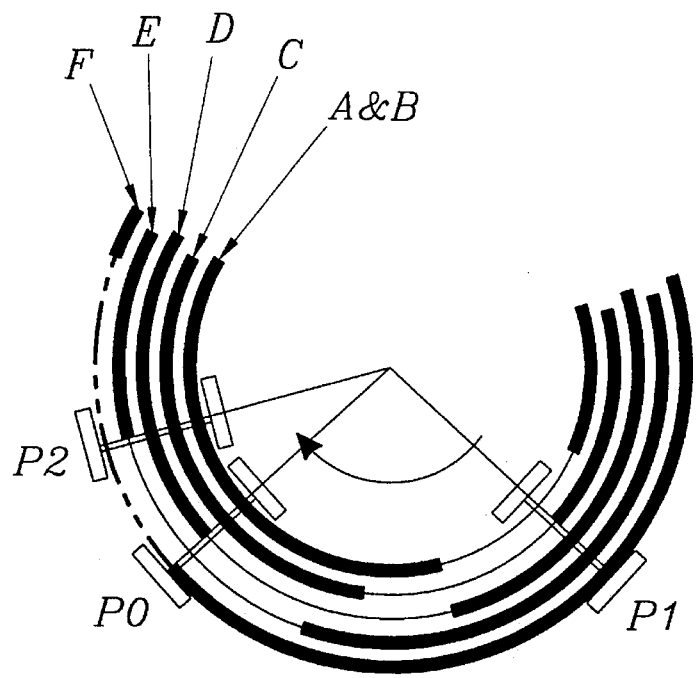
FIGS. 7a and b are schematic views of the operating positions of the valve receiving mechanism of the pump.
Figure 7B:
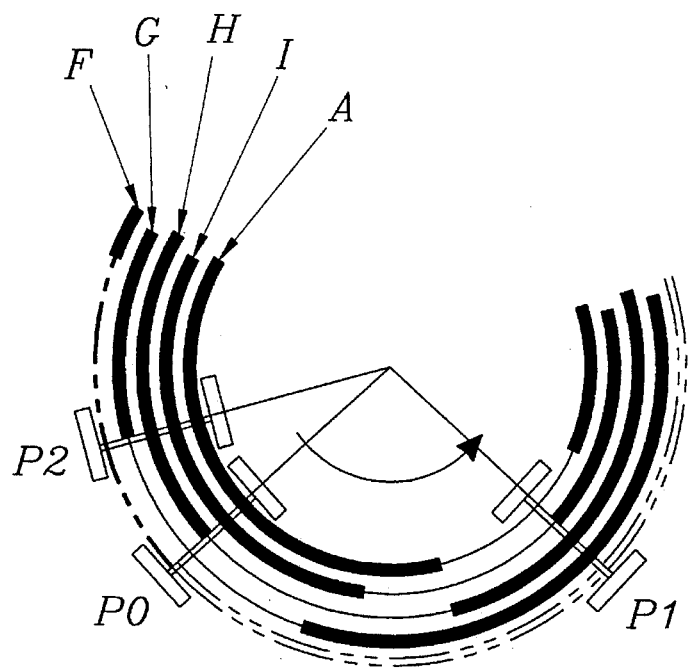

FIGS. 7a and b, a schematic of the photoelectric switches 41, 48 and 49 is shown with each position of the control flange 39 of the chuck 33 in operation described as positions A–F, with FIG. 7a showing the forward rotation (clockwise as shown) and FIG. 7b showing the return rotation (counterclockwise as shown) of the chuck 33. Position (A) describes the position of the control flange 39 when no valve is loaded into the valve receiving mechanism 32. In this position, the control flange 39 is located above all of the photoelectric switches and not operationally engaged. Position (B) corresponds to the starting position of the valve receiving mechanism 32 in which the control flange 39 interrupts the photoelectric switches 48 and 49 and leaves switch 41 open. Position (C) corresponds to the initial locking position of the pump 12 in which the control flange 39 interrupts all three photoelectric switches 41, 48 and 49. In position (D) corresponding to the flushing position, the control flange 39 interrupts photoelectric switches 49 and 41, leaving switch 48 open. In position (E) corresponding to the temporary off position, the flange 39 interrupts only microswitch 41. And finally, in position (F) corresponding to the feeding position, the flange 39 interrupts photoelectric switches 41 and 48, leaving switch 49 open.

Positions (G), (H), (I) correspond to positions (E), (D), and (C) respectively except they are entered from the return direction. In this case, (G) corresponds to the intermediate hold position, (H) corresponds to the flush position, and (I) corresponds to the lock position.

As can be seen by one of ordinary skill in the art, each position of the control flange 39 causes the photoelectric switches 41, 48 and 49 to send a unique signal to the microprocessor of the pump 12 which it can equate to the rotational position of the valve handle 22 in carrying out the desired fluid delivery by the system 10. The exact position of the control flange 39 determines the transition direction of the signal sent to the microprocessor by the photoelectric switches 41, 48 and 49.

The valve actuation unit 14 includes a fail safe default which monitors whether each rotation of the chuck 33 generates the expected signals by the photoelectric switches 41, 48 and 49. If not, the microprocessor causes the valve receiving mechanism 30 to reset to the starting position and causes the pump 12 to stop. In this manner, the valve actuation unit 14 cannot be "tricked" into initial activation by depression of the chuck 33 down to its actuation of the microswitch 40 by some device other than a valve handle 22 which holds the chuck 33 in its compressed position and the control flange 39 thereof in operational position relative to the photoelectric switches 41, 48 and 49. Should operation of the valve actuation unit be initiated by actuation of the microswitch 40, yet the chuck 33 remain in its extended position such that the control flange 39 fails to interact with the photoelectric switches 41, 48 and 49 (indicating that no valve handle 22 is positioned in the valve receiving mechanism 32) the valve receiving mechanism 32 resets to its starting position, the pump 12 stops, and the valve 19 is ejected from the valve receiving mechanism 32.

If desired, the fluid delivery system 10 of the present invention can operate with a fluid delivery set which does not include an auxiliary flushing fluid container, and therefore also does not contain the inlet tube 18. The previously described priming cycle will detect the absence of any fluid drops entering the drip chamber 23 when the valve is rotated to the flushing position for priming, and the microprocessor will then only allow the pump 12 to be programmed for delivery of the primary feeding fluid by disabling the automatic and manual flushing features of the system 10.

It will be apparent from the foregoing that, while a particular embodiment of the invention has been illustrated and described, various modifications can be made thereto without departing from the spirit and scope of the invention. Accordingly, it is not intended that the invention be limited except as by the appended claims.

We claim:

1. A valve actuation device for automatic operation of a fluid flow control valve comprising:

a valve receiving mechanism for receiving the fluid flow control valve for actuation;

a valve interface member for insuring proper orientation of the fluid flow control valve relative to said valve receiving mechanism when said fluid flow control valve is abutted against said valve receiving mechanism;

whereby, said valve receiving mechanism operates to move the valve between at least one closed position in which fluid flow through said valve is prevented to at least one open position in which fluid flow through said valve is allowed.

2. A valve actuation device according to claim 1 wherein said valve interface member allows the fluid flow control valve to be received by said valve receiving mechanism only when the fluid flow control valve is in said at least one closed position.

3. A valve actuation device according to claim 1 wherein said valve interface member allows the fluid flow control valve to be removed from said valve receiving mechanism only when the fluid flow control valve is in said at least one closed position.

4. A valve actuation device according to claim 1 wherein said valve receiving mechanism further includes a chuck member positioned to contact a handle of the fluid flow control valve when properly positioned within said valve receiving mechanism, and an activation switch for activating rotation of said chuck;

whereby, proper positioning of the fluid flow control valve within said valve receiving mechanism causes said chuck to contact said activation switch and rotate the valve handle to said at least one open position.

5. A valve actuation device according to claim 4 wherein said valve receiving mechanism and said valve interface member operate to retain the valve handle within said valve receiving mechanism whenever said valve receiving mechanism has operated to move the valve handle to said at least one open position.

6. A valve actuation device according to claim 1 wherein said valve interface member is detachable from said valve actuation device.

7. A valve actuation device according to claim 6 wherein detachment of said valve interface member exposes at least a portion of said valve receiving mechanism.

8. A valve actuation device according to claim 1 further including means for operating the fluid flow control valve between at least two closed positions in which fluid flow through the fluid flow control valve is prevented and at least one open position in which fluid flow through the fluid flow control valve is allowed.

9. A valve actuation device according to claim 8 wherein said means for operating the fluid flow control valve includes a rotational member and movement of the fluid flow control valve between said closed positions and said open positions includes rotation of said valve receiving mechanism.

10. A valve actuation device according to claim 9 wherein said rotational member of said operating means rotates through each of said closed positions and said open positions in a rotational arc of approximately 120 degrees.

11. A valve actuation device according to claim 10 wherein each of said closed positions and said open positions are spaced approximately 30 degrees apart.

12. A fluid delivery system including a fluid delivery set having a valve and including a pump having a pumping unit and a valve actuation unit, said valve actuation unit comprising:

a valve receiving mechanism for receiving the valve for actuation;

a valve interface member for ensuring proper orientation of the valve relative to said valve receiving mechanism when said valve is abutted against said valve receiving mechanism;

whereby, said valve receiving mechanism operates to move the valve between at least one closed position in which fluid flow through said valve is prevented to at least one open position in which fluid flow through said valve is allowed.

13. A fluid delivery system according to claim 12 wherein said valve interface member allows the fluid flow control valve to be received by said valve receiving mechanism only when the fluid flow control valve is in said at least one closed position.

14. A fluid delivery system according to claim 12 wherein said valve interface member allows the fluid flow control valve to be removed from said valve receiving mechanism only when the fluid flow control valve is in said at least one closed position.

15. A fluid delivery system according to claim 12 wherein said valve receiving mechanism further includes a chuck member positioned to contact a handle of the fluid flow control valve when properly positioned within said valve receiving mechanism, and an activation switch for activating rotation of said chuck;

whereby, proper positioning of the fluid flow control valve within said valve receiving mechanism causes said chuck to contact said activation switch and rotate the valve handle to said at least one open position.

16. A fluid delivery system according to claim 15 wherein said valve receiving mechanism and said valve interface member operate to retain the valve handle within said valve receiving mechanism whenever said valve receiving mechanism has operated to move the valve handle to said at least one open position.

17. A fluid delivery system according to claim 12 wherein said valve interface member is detachable from said valve actuation device.

18. A fluid delivery system according to claim 17 wherein detachment of said valve interface member exposes at least a portion of said valve receiving mechanism.

19. A valve actuation device according to claim 1 further including means for operating the fluid flow control valve between at least two closed positions in which fluid flow through the fluid flow control valve is prevented and at least one open position in which fluid flow through the fluid flow control valve is allowed.

20. A fluid delivery system according to claim 19 wherein said means for operating the fluid flow control valve includes a rotational member and movement of the fluid flow control valve between said closed positions and said open position includes rotation of said valve receiving mechanism.

21. A fluid delivery system according to claim 20 wherein said rotational member of said operating means rotates through each of said closed positions and said open positions in a rotational arc of approximately 120 degrees.

22. A fluid delivery system according to claim 21 wherein each of said closed positions and said open positions are spaced approximately 30 degrees apart.

23. A fluid delivery system according to claim 12 wherein said means for operating the fluid flow control valve further includes means for operating the fluid flow control valve between at least three closed positions in which fluid flow through the fluid flow control valve is prevented and at least two open positions in which fluid flow through the fluid flow control valve is allowed.

24. A fluid delivery system according to claim 23 wherein said system further includes a pump control mechanism for controlling the fluid flow rate through said valve, said control mechanism being operatable to change fluid flow rates through said valve at each of said at least two open positions of said valve.

* * * * *